US009320544B2

(12) United States Patent
Black

(10) Patent No.: US 9,320,544 B2
(45) Date of Patent: Apr. 26, 2016

(54) DYNAMIC SPINE STABILIZERS

(71) Applicant: GLOBUS MEDICAL, INC., Audobon, PA (US)

(72) Inventor: Michael Black, Swarthmore, PA (US)

(73) Assignee: GLOBUS MEDICAL, INC., Audubon, PA (US)

(*) Notice: Subject to any disclaimer, the term of this patent is extended or adjusted under 35 U.S.C. 154(b) by 0 days.

(21) Appl. No.: 13/921,545

(22) Filed: Jun. 19, 2013

(65) Prior Publication Data

US 2014/0052185 A1    Feb. 20, 2014

Related U.S. Application Data

(62) Division of application No. 12/635,819, filed on Dec. 11, 2009, now Pat. No. 8,491,638.

(51) Int. Cl.
*A61B 17/70*    (2006.01)

(52) U.S. Cl.
CPC ........... *A61B 17/7011* (2013.01); *A61B 17/701* (2013.01); *A61B 17/702* (2013.01); *A61B 17/7005* (2013.01); *A61B 17/7007* (2013.01); *A61B 17/7008* (2013.01); *A61B 17/7014* (2013.01); *A61B 17/7025* (2013.01); *A61B 17/7026* (2013.01); *A61B 17/7031* (2013.01); *A61B 17/7043* (2013.01); *A61B 17/7038* (2013.01)

(58) Field of Classification Search
CPC ........... A61B 17/7011; A61B 17/7005; A61B 17/7007; A61B 17/7008; A61B 17/701; A61B 17/7014; A61B 17/702; A61B 17/7025; A61B 17/7026; A61B 17/7031; A61B 17/7043; A61B 17/7038
USPC ......... 606/246, 250–253, 257–259, 264, 265, 606/267, 270, 272, 277, 279; 623/17.11
See application file for complete search history.

(56) References Cited

U.S. PATENT DOCUMENTS

| 5,470,333 A * | 11/1995 | Ray .............................. 606/261 |
| 6,585,738 B1 * | 7/2003 | Mangione et al. ............ 606/258 |
| 7,294,129 B2 | 11/2007 | Hawkins |
| 7,985,223 B2 * | 7/2011 | Khodadadyan-Klostermann et al. ............................... 606/71 |
| 2006/0247635 A1 | 11/2006 | Gordon |
| 2006/0271046 A1 | 11/2006 | Kwak |

* cited by examiner

*Primary Examiner* — Pedro Philogene
*Assistant Examiner* — David C Comstock

(57) ABSTRACT

Treatment of spinal irregularities, including, in one or more embodiments, dynamic spine stabilizers and systems that can be used to stabilize one or more motion segments in a patient's spine. Spine stabilization systems may comprise a first bone fastener configured to attach the spine stabilization system to a first vertebra. Spine stabilization systems further may comprise a second bone fastener configured to attach the spine stabilization system to a second vertebra. Spine stabilization systems further may comprise a dynamic spine stabilizer configured to connect the first bone fastener and the second bone fastener with at least some relative movement between the first bone fastener and the second bone fastener.

12 Claims, 13 Drawing Sheets

DYNAMIC SPINE STABILIZERS

CROSS-REFERENCE TO RELATED APPLICATIONS

The present application is a divisional application of U.S. patent application Ser. No. 12/635,819 filed on Dec. 11, 2009, which is incorporated by reference herein.

FIELD OF THE INVENTION

The present disclosure generally relates to treatment of spinal irregularities. In particular, in one or more embodiments, the present disclosure relates to dynamic spine stabilizers and systems that can be used to stabilize one or more motion segments in a patient's spine.

BACKGROUND

The spine includes a series of joints routinely called motion segment units, which is the smallest component of the spine that exhibits kinematic behavior characteristic of the entire spine. The motion segment unit is capable of flexion, extension, lateral bending and translation. The components of each motion segment unit include two adjacent vertebrae and their apophyseal joints, the intervertebral disc, and the connecting ligamentous tissue. Each component of the motion segment unit contributes to the mechanical stability of the joint.

Components of a motion segment that move out of position or become damaged can lead to serious pain and may lead to further injury to other components of the spine. Depending upon the severity of the structural changes that occur, treatment may include fusion, discectomy, or laminectomy.

Underlying causes of structural changes in the motion segment unit leading to instability include trauma, degeneration, aging, disease, surgery, and the like. Thus, rigid stabilization of one or more motion segment units may be an important element of a surgical procedure in certain cases (e.g., injuries, deformities, tumors, etc.), whereas it is a complementary element in others (e.g., fusion performed due to degeneration). The purpose of rigid stabilization is the immobilization of a motion segment unit Rigid stabilization typically results in a rigid, internal fixation of all or part of intervertebral joints and usually involves metallic rods, screws, plates, and the like for stabilization. In general, the devices are intended to immobilize the motion segment.

In addition to a loss of mobility, total immobilization of the motion segment also can cause unloading of the disk. This can undesirably impact fusion, for example, slowing or even reducing the growth of bone into our through an implant placed into the disc space. Additionally, unloading of the disc can lead to further degeneration of the disk in the immobilized motion segment. Another drawback is that total immobilization also can cause the mobility of the motion segment to be transferred to other motion segments of the spine. The added stresses transferred to motion segments neighboring or nearby the immobilized segment can cause or accelerate the degeneration of those segments.

Thus, there is a need for improved systems that can stabilize motion segments with reduced degeneration of neighboring joints with faster and more substantial fusion.

SUMMARY

An embodiment of the present invention provides a spine stabilization system. The spine stabilization system may comprise a first bone fastener configured to attach the spine stabilization system to a first vertebra. The spine stabilization system further may comprise a second bone fastener configured to attach the spine stabilization system to a second vertebra. The spine stabilization system further may comprise a dynamic spine stabilizer configured to connect the first bone fastener and the second bone fastener with at least some relative movement between the first bone fastener and the second bone fastener.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

These drawings illustrate certain aspects of the present invention and should not be used to limit or define the invention.

DETAILED DESCRIPTION OF THE ILLUSTRATED EMBODIMENTS

The present invention is generally directed to dynamic spine stabilizers and systems that can be used to stabilize one or more motion segments in a patient's spine. Instead of completely immobilizing the motion segment, embodiments of the dynamic spine stabilizers allow for at least some movement of the motion segment. By way of example, the dynamic spine stabilizers may allow for bending (angular) and/or axial (translational) movement. While embodiments of the dynamic spine stabilizers may be particularly suited for posterior cervical stabilization, it should be understood that the stabilizers may be used on the cervical, thoracic, lumbar, and sacral segments of the spine. In addition, the stabilizers may be used with the anterior, antero-lateral, lateral, and/or posterior portions of at least one motion segment.

Figure 1:
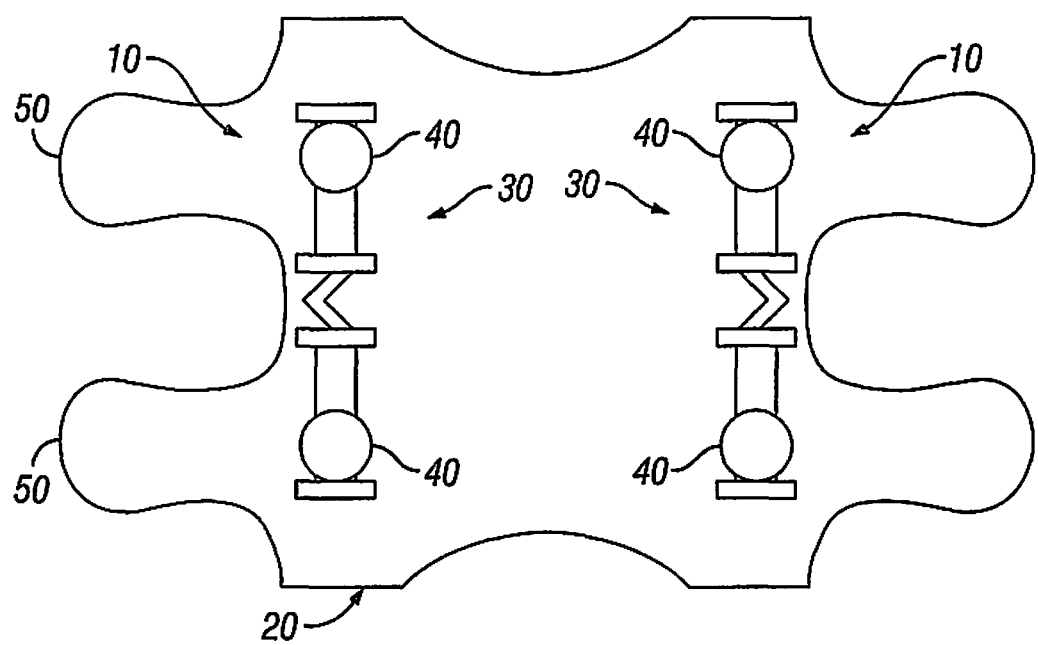
FIG. 1 illustrates a stabilized motion segment in accordance with one embodiment of the present invention.

FIG. 1 illustrates a pair of dynamic spine stabilization systems 10 implanted in a patient's spine for stabilizing a motion segment 20 in accordance with one embodiment of the present invention. While only one pair of dynamic spine stabilization systems 10 are illustrated, it should be understood that more than two dynamic spine stabilization systems 10 can be implanted into a patient's spine as desired for a particular procedure. In addition, while the pair of dynamic spine stabilization systems 10 is illustrated on either side of the motion segment 20, it should be understood that two or more spine stabilization systems 10 may be placed on one side of the patient's spine for stabilization. For example, additional spine stabilization systems 10 may be placed along the spine superior or inferior to the motion segment 20. Moreover, one or more stabilization systems that incorporate a rigid rod—rather than a dynamic stabilizer—may also be used in conjunction with the dynamic spine stabilization systems 20. It should be understood that suitable transverse rods may also be incorporated to link the dynamic spine stabilization systems 10 on either side of the motion segment 20.

As illustrated, each of the dynamic spine stabilization systems 10 may include a dynamic stabilizer 30 coupled to the bone fasteners 40. The dynamic stabilizer 30 advantageously provides stabilization while providing at least some movement of the motion segment 20. By way of example, the dynamic stabilizer 30 should provide for relative movement between the adjacent vertebrae 50. The bone fasteners 40 generally should fix the pair of dynamic spine stabilization systems 10 to the adjacent vertebrae 50. Suitable bone fasteners 40 may include any of a variety of fasteners that may be coupled to the dynamic stabilizer 30 while remaining securely fastened to the intended bone. Thus, examples of suitable bone fasteners 40 include polyaxial screws, helical blades, expandable screws, such as Mollie bolt type fasteners, which are inserted or screwed into the bone and expanded by way of some type of expansion mechanism, conventional pedicle screws, staples, hooks, and the like.

Figure 2:
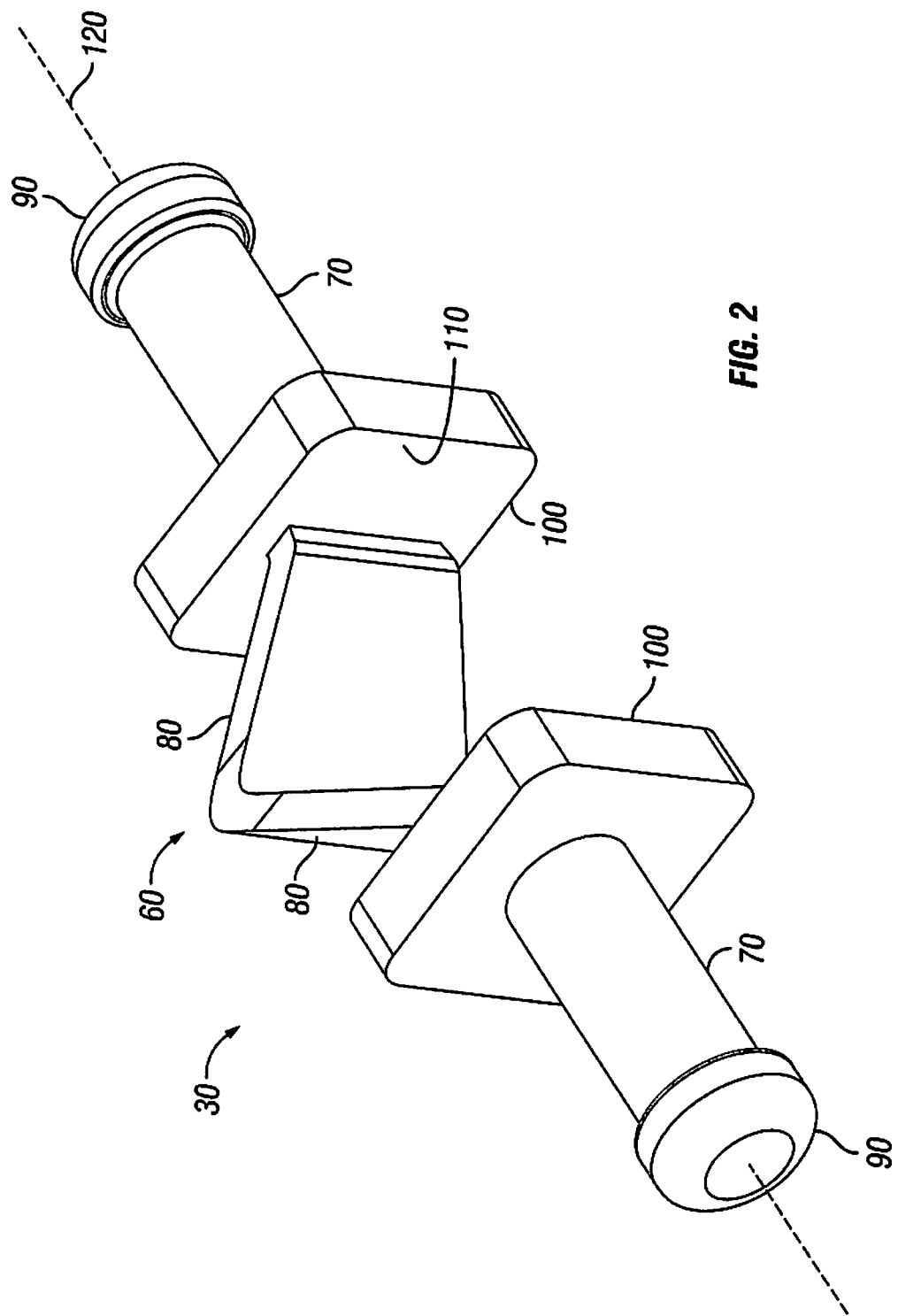
FIG. 2 is a perspective view of a dynamic spine stabilizer incorporating a spring in accordance with one embodiment of the present invention.

FIG. 2 illustrates dynamic stabilizer 30 in accordance with one embodiment of the present invention. As illustrated, the dynamic stabilizer 30 comprises a spring 60 disposed between rod portions 70. In an embodiment, the spring 60 is in the general shape of a V having, for example, legs 80 with a rectangular cross section. The rod portions 70 may be configured and adapted for insertion into rod-receiving members of corresponding bone fasteners. In an embodiment (not illustrated), the rod portions 70 may be inserted into a rod-receiving member (e.g., a side-loading head, top-loading head, eye-hole loading head, etc.) of a polyaxial screw. After insertion, a locking element (e.g., a clamping screw) may be placed onto the head to secure the rod portions 70 in the rod receiving member of the respective bone fastener. One end of the rod portions 70 may comprise a cap 90, such as a flanged end. The other end of the rod portions 70 may comprise an end plate 100. As illustrated, the end of each leg 80 may extend to the corresponding end plate 100. In an embodiment, the end of each leg 80 may be fixed to a face 110 of the end plate 100.

In accordance with embodiments of the present invention, the dynamic stabilizer 30 should allow for relative movement between bone fasteners (not illustrated) coupled to the rod portions 70. By way of example, if a force is applied in a direction of the longitudinal axis 120 of the dynamic stabilizer 30 to move the rod portions 70 towards one another, the spring 60 should be deformed. When the force is removed, the spring 60 should return to its original position. In addition, the rod portions 70 can also rotate with respect to each other if a rotational force is applied about longitudinal axis 120. Moreover, the rod portions 70 can also be axially displaced if a force is applied in a direction perpendicular to the longitudinal axis 120.

The components of the dynamic stabilizer 30 may be made from a variety of biocompatible materials, including metals, ceramic materials, and polymers. Examples of biocompatible materials include titanium, stainless steel, aluminum, cobalt-chromium, alloys, polyetheretherketones ("PEEK"), and polyethylene. In an embodiment, the spring 60 may be made from titanium or a titanium alloy.

Figure 3:
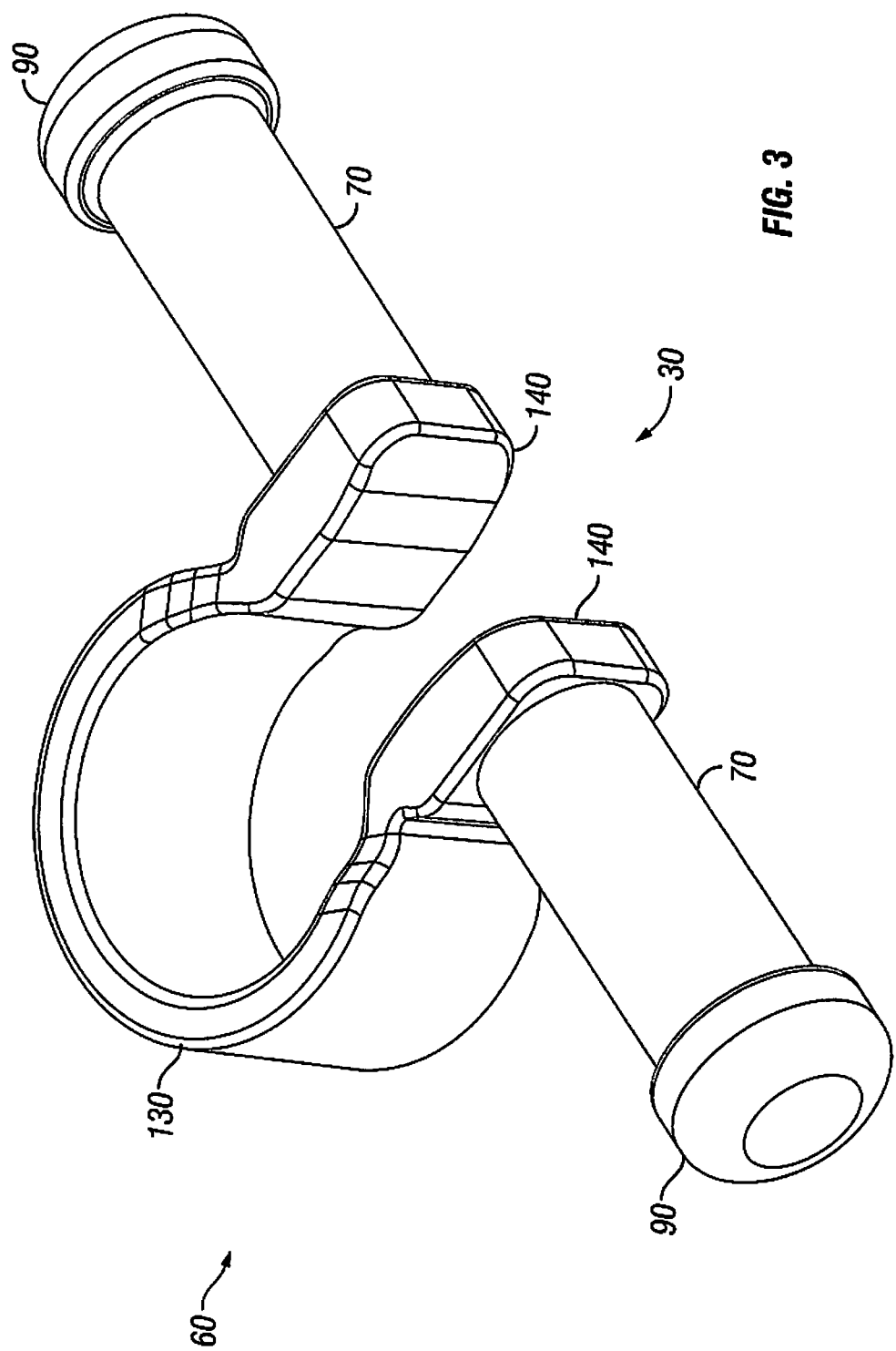
FIG. 3 is a perspective view of a dynamic spine stabilizer incorporating a spring in accordance with another embodiment of the present invention.

FIG. 3 illustrates dynamic stabilizer 30 in accordance with another embodiment of the present invention. The illustrated dynamic stabilizer 30 is similar to the embodiment of FIG. 2, in that the dynamic stabilizer 30 comprises a spring 60 disposed between rod portions 70. However, unlike the spring 60 of FIG. 2 in the general shape of a V, FIG. 3 illustrates a spring 60 that is semi-elliptical in shape. The spring 60 may be rectangular in cross section, for example. In an embodiment, the spring 60 is a semi-elliptical leaf spring. As illustrated, the spring 60 may have a semi-elliptical portion 130 and rod-connecting portions 140 that extend from either end of the semi-elliptical portion 130. In an embodiment, the rod-connection portions 140 may be generally parallel plates that extend from either end of the semi-elliptical portion 130. The rod portions 70 may be configured and adapted for insertion into rod-receiving members of corresponding bone fasteners. One end of the rod portions 70 may comprise a cap 90, such as a flanged end. The other ends of the prod portions 70 may be coupled to the rod-connecting portions 140 of the spring 60.

Figure 4:
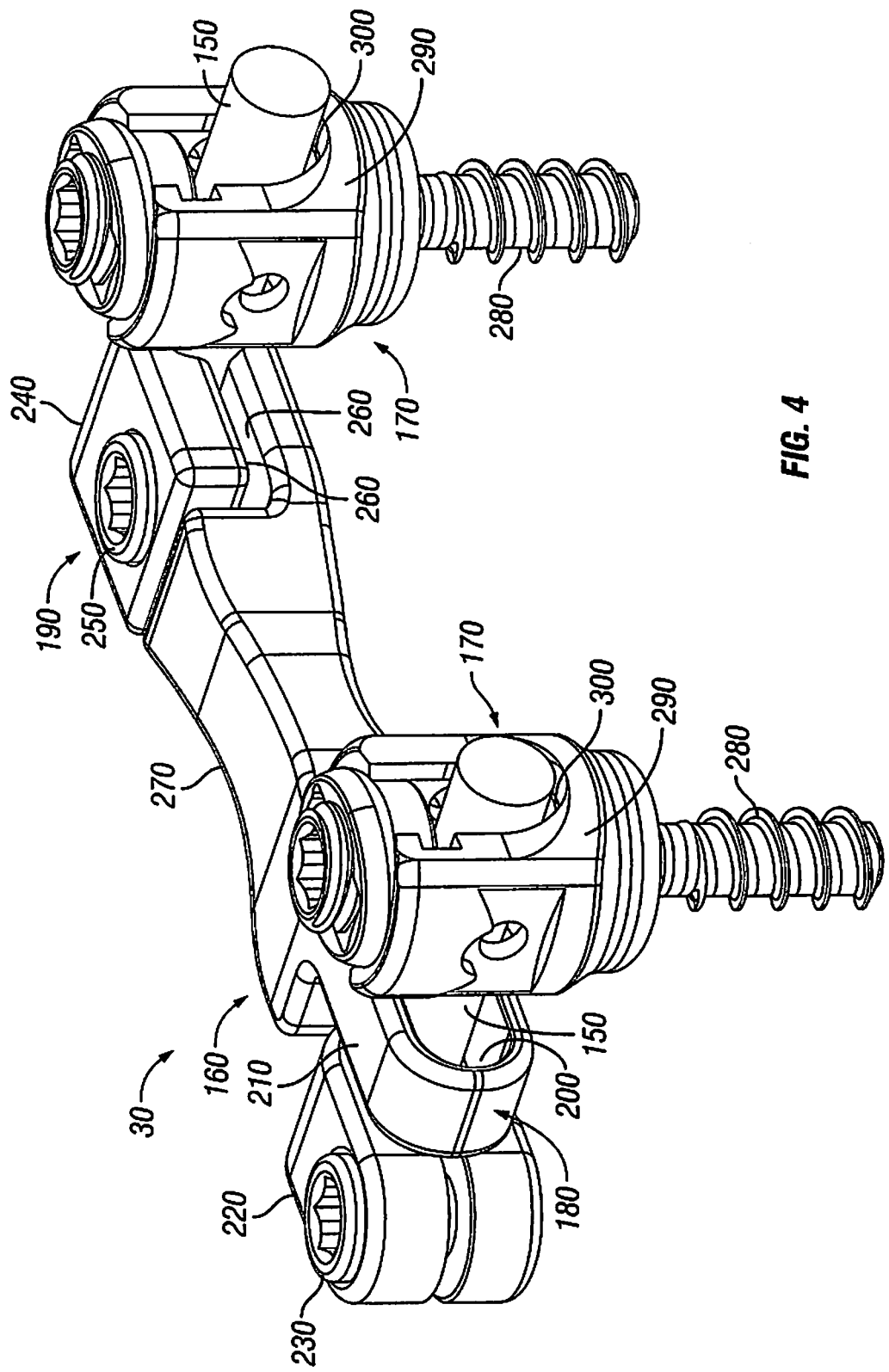
FIGS. 4-6 are perspective, end and top views of a dynamic spine stabilizer laterally offset from the bone fasteners in accordance with one embodiment of the present invention.
Figure 6:
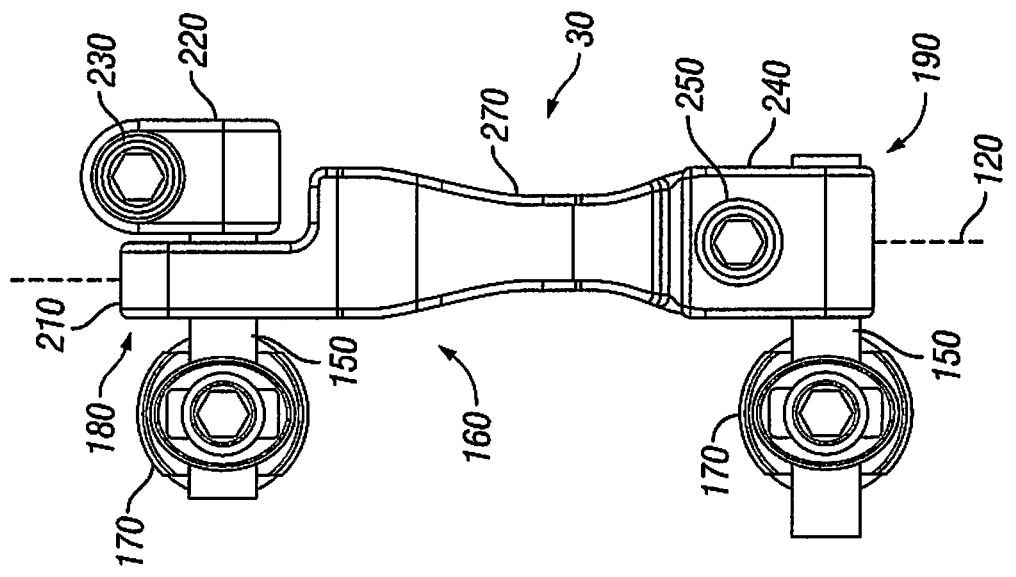
Figure 5:
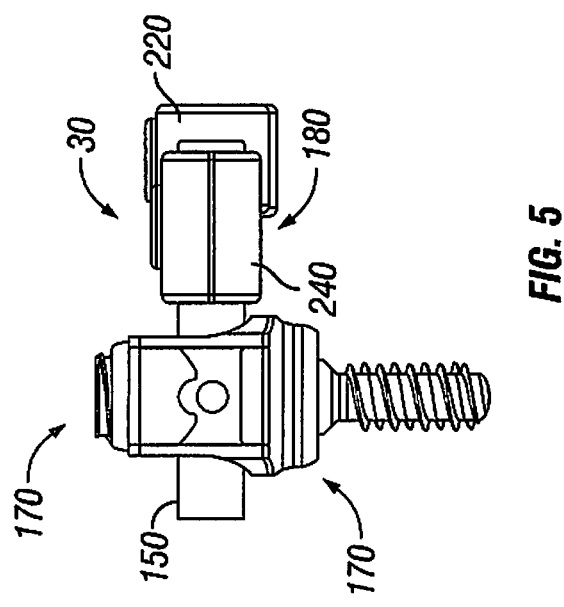

FIGS. 4-6 illustrate dynamic stabilizer 30 that is laterally offset in accordance with one embodiment of the present invention. As illustrated, dynamic stabilizer 30 comprises lateral rods 150 coupled by cross member 160. Each of the lateral rods 150 may be secured to a corresponding pedicle screw 170. The lateral rods 150 may extend in a generally parallel direction from the pedicle screws 170. As illustrated, the lateral rods 150 may be coupled by cross member 160 that extends generally transverse to the lateral rods 150. In the illustrated embodiment, the cross member 160 comprises a translatable end 180 and a rod-locking end 190. The translatable end 180 may be configured and adapted to slidably engage one of the lateral rods 150. In other words, the translatable end 180 may couple the cross member 160 to the lateral rod 150 while still allowing for relative movement between the cross member 160 and the lateral rod 150. As illustrated, the translatable end 180 may have an opening 200 through which one of the lateral rods 150 may be disposed. In an embodiment, the translatable end 180 has a yoke 210 that may be disposed over one of the lateral rods 150. As illustrated, the yoke 210 may define the opening 200. To secure the translatable end 180 on the lateral rod 150, a first clamp 220 may be placed on one end of the lateral rod 150. In an embodiment, first screw 230 may be tightened to lock the first clamp 220 onto the lateral rod 150. As illustrated, the translatable end 180 may be disposed over the lateral rod 150 between the pedicle screw 170 and the first clamp 220. In an embodiment, the translatable end 180 may freely move between the pedicle screw 170 and the first clamp 220.

The rod-locking end 190 may be fixedly coupled to the other one of the lateral rods 150. As illustrated, the rod-locking end 190 may be configured and adapted with a seat that receives the corresponding rod 150. The rod-locking end 190 may be locked or otherwise tightened to secure the lateral rod 150 in the seat. In the illustrated embodiment, the rod-locking end 190 is configured in the shape of a clamp, e.g., second clamp 240. The second clamp 240 may define the seat that receives the lateral rod 150. Second screw 250 may be tightened, for example, to lock opposing surfaces 260 of the second clamp 240 down onto the lateral rod 150.

A tapered segment 270 may connect the translatable end 180 and the rod-locking end 190. As illustrated, the tapered segment 270 may have a gradual reduction in thickness from either end to its middle. In an embodiment, the tapered segment 270 may be generally rectangular in cross section. In another embodiment (not illustrated), tapered segment 270 may be generally elliptical or circular in cross section.

As illustrated by FIG. 4, the lateral rods 150 may be secured to a corresponding pedicle screw 170. The pedicle screw 170 may comprise a threaded shaft 280 for fixation into a bone and a head 290. The head 290 generally may comprise a recess 300 for receiving a rod, e.g., lateral rods 150. In an embodiment, the recess 300 extends away from the threaded shaft 280. In an embodiment, the head 290 is top loading. In an alternative embodiment (not illustrated), the recess 300 may extend perpendicular to the threaded shaft 280 such that the head 290 may be side loading. One of the lateral rods 150 can be placed into the recess 300. A locking element 310 (e.g., a nut) can be threaded into the top of the head 290 to secure one of the lateral rods 150 in a corresponding recess 300.

In accordance with embodiments of the present invention, the dynamic stabilizer 30 illustrated by FIGS. 4-6 should allow for relative movement between the pedicle screws 70. By way of example, if a force is applied in a direction of the longitudinal axis 120 of the dynamic stabilizer 30, the opening 200 in the yoke 210 may be sized to allow movement of the dynamic stabilizer 30 along its longitudinal axis 120. In addition, the translatable end 180 can also slide along the lateral rod 150, for example, if a force is applied in a direction perpendicular to longitudinal axis 120. Moreover, the translatable end 180 should also be configured to rotate with respect to the lateral rod 150 over which it is disposed.

Figure 7:
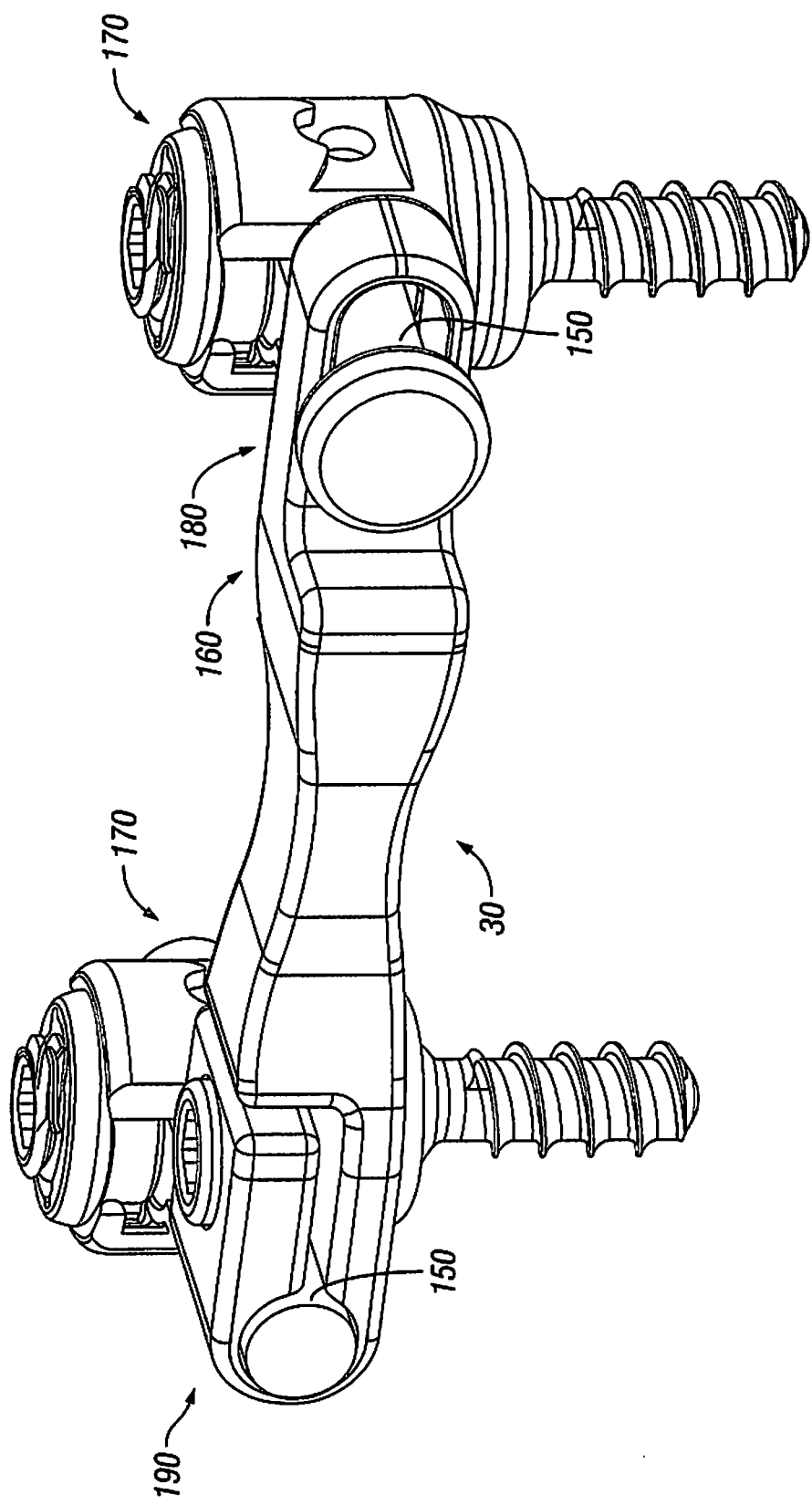
FIGS. 7-9 are perspective, end and top views of a dynamic spine stabilizer laterally offset from the bone fasteners in accordance with another embodiment of the present invention.
Figure 9:
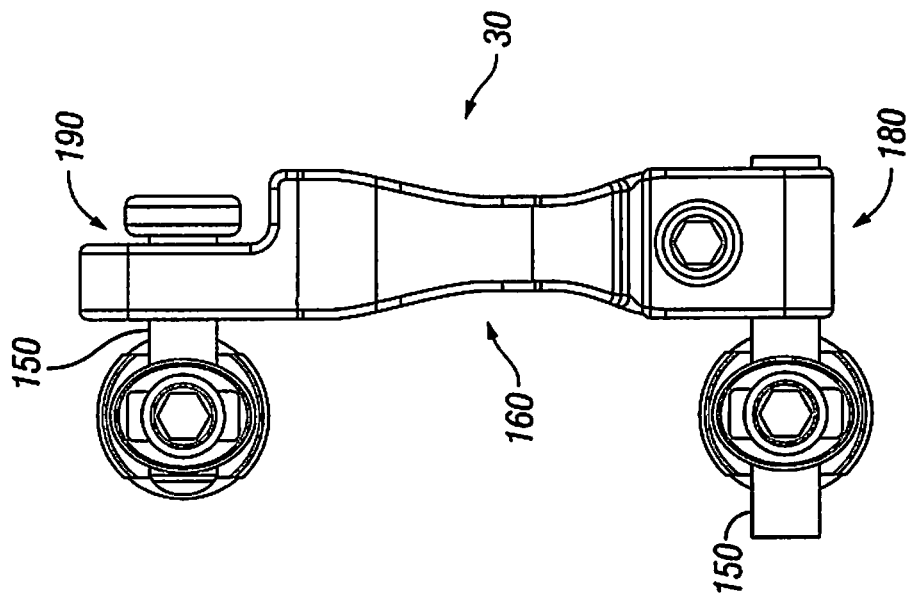
Figure 8:
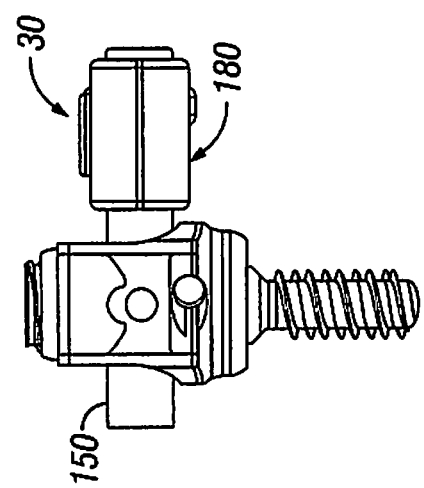

FIGS. 7-9 illustrate dynamic stabilizer 30 that is laterally offset in accordance with one embodiment of the present invention. The illustrated dynamic stabilizer 30 is similar to the embodiment of FIGS. 4-6, in that the dynamic stabilizer 30 is laterally offset. For example, the dynamic stabilizer 30 comprises lateral rods 150 coupled by cross member 160. Each of the lateral rods 150 may be secured to a corresponding pedicle screw 170. In the illustrated embodiment, the cross member 160 comprises a translatable end 180 and a rod-locking end 190. As illustrated, the translatable end 180 may be disposed over one of the lateral rods 150. However, unlike the first clamp 220 of FIG. 4, the lateral rod 150 comprises a flanged end 320 for securing the translatable end 10 onto the lateral rod 150. It should be understood that other suitable mechanisms may be also used to secure the translatable end 180 onto the lateral rod 150 while allowing for the desired movement.

Figure 10:
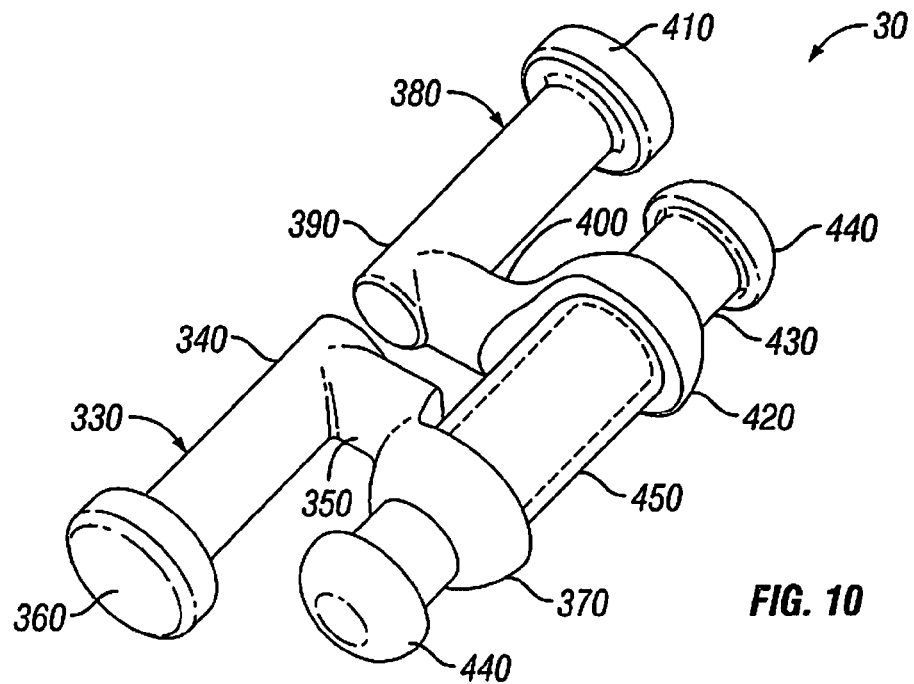
FIGS. 10-11 are perspective views of a dynamic spine stabilizer laterally offset from the bone fasteners in accordance with another embodiment of the present invention.

FIG. 10 illustrates dynamic stabilizer 30 that is laterally offset in accordance with another embodiment of the present invention. In the illustrated embodiment, the dynamic stabilizer 30 comprises first bent rod portion 330. In an embodiment, the first bent rod portion 330 may be made from a material that comprises PEEK. As illustrated, the first bent rod portion 330 generally may comprise first rod segment 340 and second rod segment 350 extending from one end of first rod segment 340. In an embodiment, the second rod segment 350 extends transverse from one end of the first rod segment 340. The other end of the first rod segment 340 may have a cap 360. In an embodiment, the cap 360 is a flanged end. The first rod segment 340 may generally be configured and adapted for insertion into a rod-receiving member of a bone fastener. The first bent rod portion 330 further may comprise rod connecting end 370. In an embodiment, the rod connecting end 370 may have a generally ring-shaped opening for receiving a rod.

As illustrated, the dynamic stabilizer 30 further may comprise second bent rod portion 380. In an embodiment, the second bent rod portion 380 may be made from a material that comprises PEEK. The second bent rod portion 380 generally may comprises first rod segment 390 and second rod segment 400 extending from one end of first rod segment 390. In an embodiment, the second rod segment 400 extends transverse from one end of the first rod segment 390. The other end of the first rod segment 390 may have a cap 410. In an embodiment, the cap 410 is a flanged end. The first rod segment 390 may generally be configured and adapted for insertion into a rod-receiving member of a bone fastener. The second bent rod portion 380 further may comprise rod connecting end 420. In an embodiment, the rod connecting end 420 may have a generally ring-shaped opening for receiving a rod. As illustrated, the first bent rod portion 330 and the second bent rod portion 340 may be aligned with mirror-like symmetry such that the second rod segments 350, 400 are generally parallel.

In the illustrated embodiment, the dynamic stabilizer 30 further may comprise cross member 430. In an embodiment, the cross member 430 may be made from a material that comprises PEEK. The cross member 430 may be rod-like in shape. As illustrated, the cross member 430 may extend between the rod connecting ends 370, 420 with the rod connecting ends 370, 420 disposed over the cross member 430. As illustrated, the rod connecting ends 370, 420 may be generally ring shaped and extend around the cross member 430. In an embodiment, each of the rod connecting ends 370, 420 is slidable along the cross member 430 and rotatable about the cross member 430. As illustrated, a spacer 450 may be disposed over the cross member 430 between the rod connecting ends. In an embodiment, the spacer 450 may be a cylindrically shaped sleeve. In an embodiment, the spacer 450 may made from a flexible material, such as polyethylene terephthalate. Caps 440 may be disposed on either end of the cross member 430. In an embodiment, the caps 440 may be flanged ends.

Figure 11:
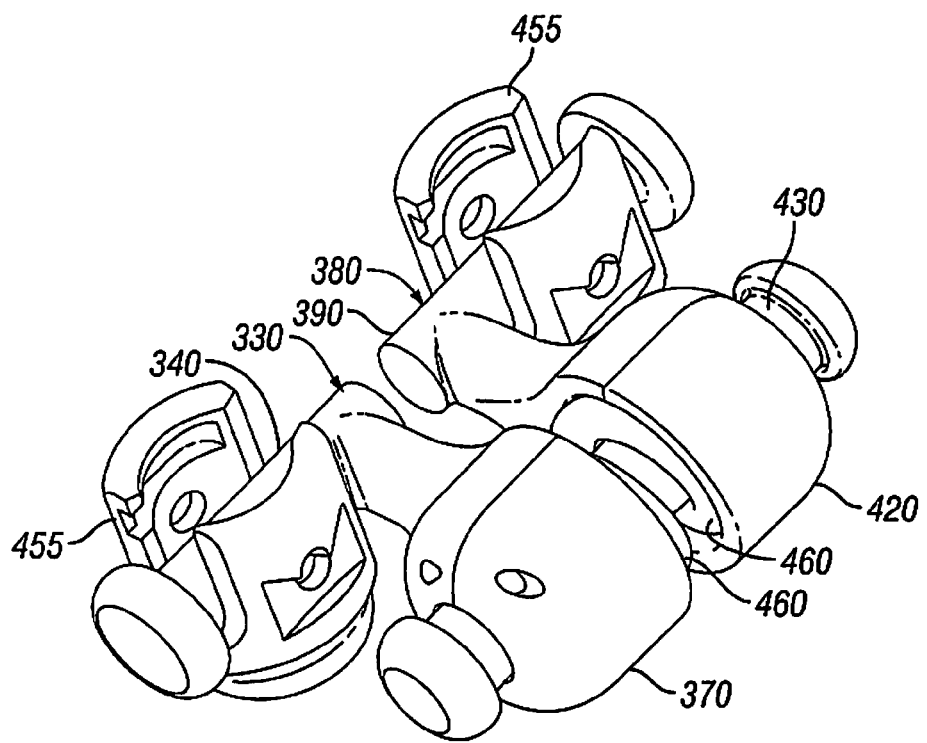

FIG. 11 illustrates dynamic stabilizer 30 that is laterally offset in accordance with another embodiment of the present invention. The illustrated dynamic stabilizer 30 is similar to the embodiment of FIG. 10, in that the dynamic stabilizer 30 is laterally offset. For example, the dynamic stabilizer 30 comprises first and second bent rod portions 330, 380. As illustrated, the first and second bent rod portions 330, 380 may each comprise first rod segments 340, 390 for insertion into rod receiving member of a bone fastener, such as slots in head 445 of a bone fastener. In an embodiment, cross member 430 may be disposed between the rod connecting ends 370, 420 of the first and second bent rod portions 330, 380. However, rather than having the spacer 450 of FIG. 10 disposed between the rod connecting ends 370, 420, the embodiment of FIG. 11 comprises two ring-shaped members 460 disposed over the cross member 430. As illustrated, the each of the rod connecting ends 370, 420 may surround a corresponding ring-shaped member 460. In an embodiment, the ring-shaped members 460 may be made from a material that comprises titanium, carbon fiber and/or PEEK.

Figure 12:
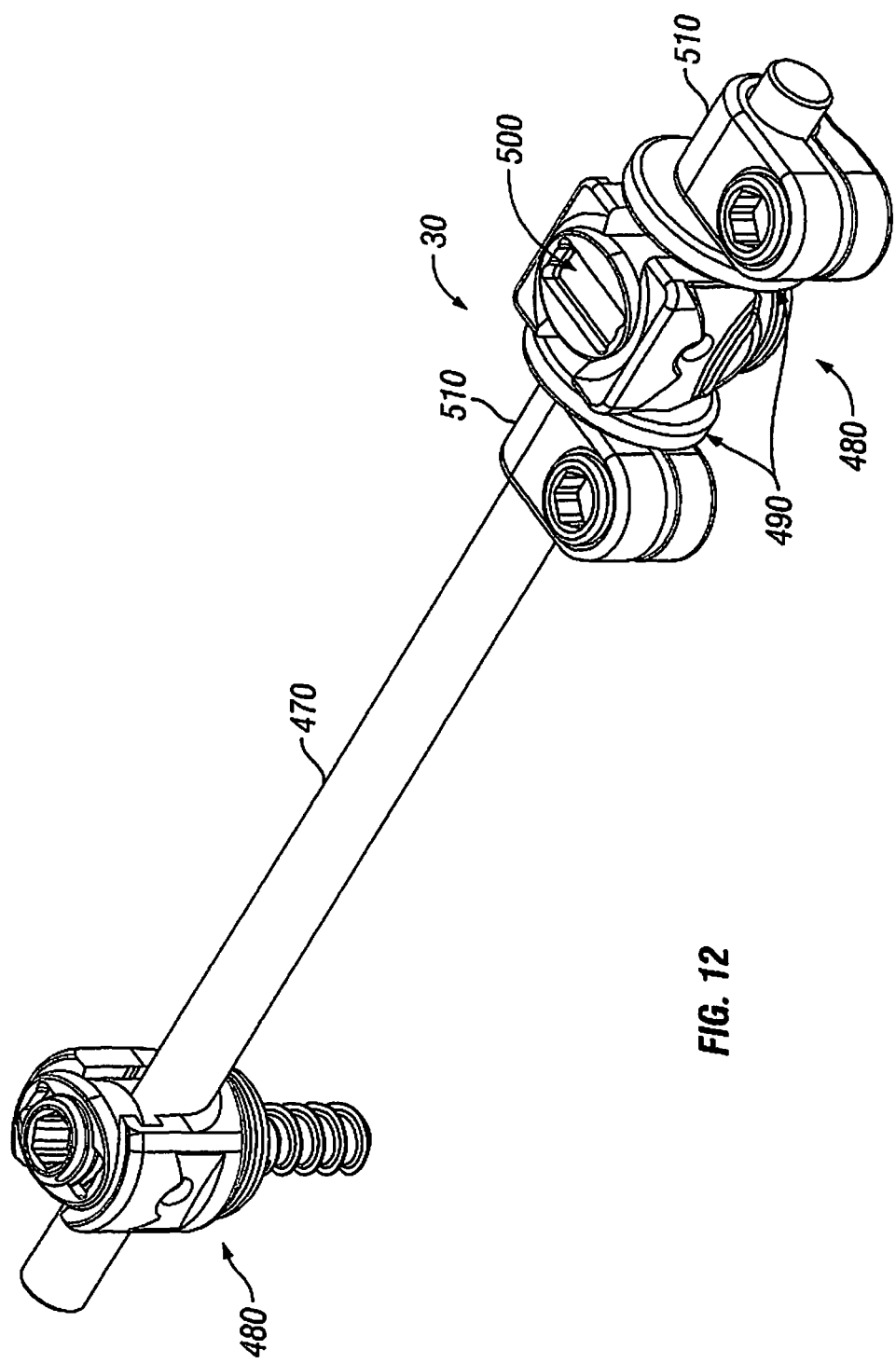
FIG. 12 is a perspective view of a dynamic spine stabilizer incorporating one or more spring washers in accordance with one embodiment of the present invention.

FIG. 12 illustrates dynamic stabilizer 30 in accordance with one or more embodiments of the present invention. As illustrated, a cross member, such as rod 470 may be disposed between pedicle screws 480. To stabilize the rod 470 while allowing for relative movement between the pedicle screws 480, the dynamic stabilizer 30 may comprise spring washers 490 disposed on either side of a translatable locking cap 500. The translatable locking cap 500 should be able to secure the rod 470 to one of the pedicle screws 480 while allowing for some movement with respect to the threaded portion of the corresponding pedicle screw 480. Clamps 490 may be placed on cross member 430 to secure the spring washers 470 against the translatable locking cap 480. As illustrated, one of the spring washers 470 is disposed between each of the clamps 490 and the translatable locking cap 480.

Figure 13:
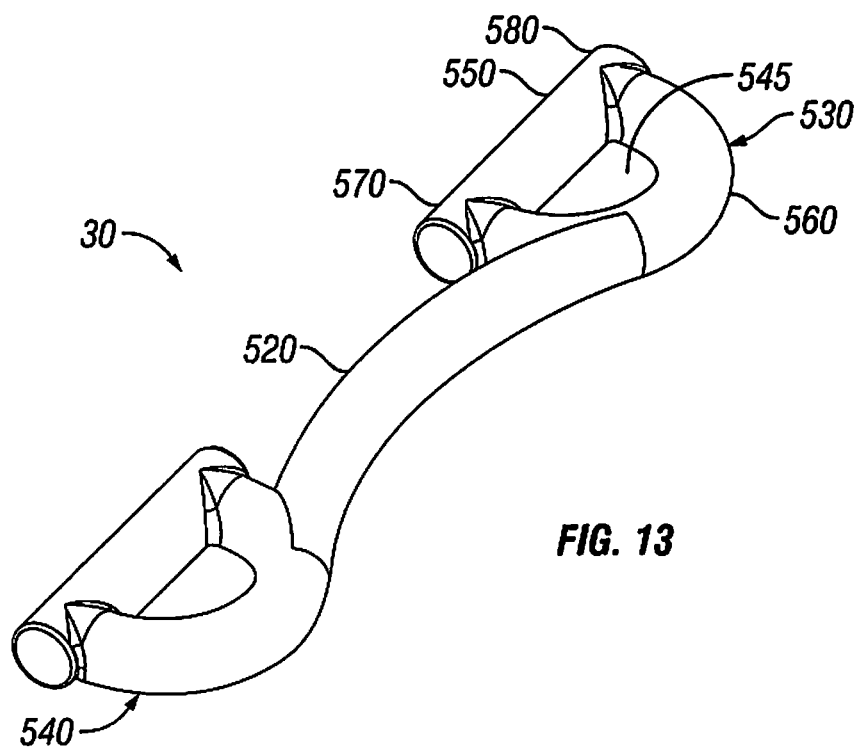
FIG. 13 is a perspective view of a dynamic spine stabilizer incorporating a concave bowed segment in accordance with one embodiment of the present invention.
Figure 14:
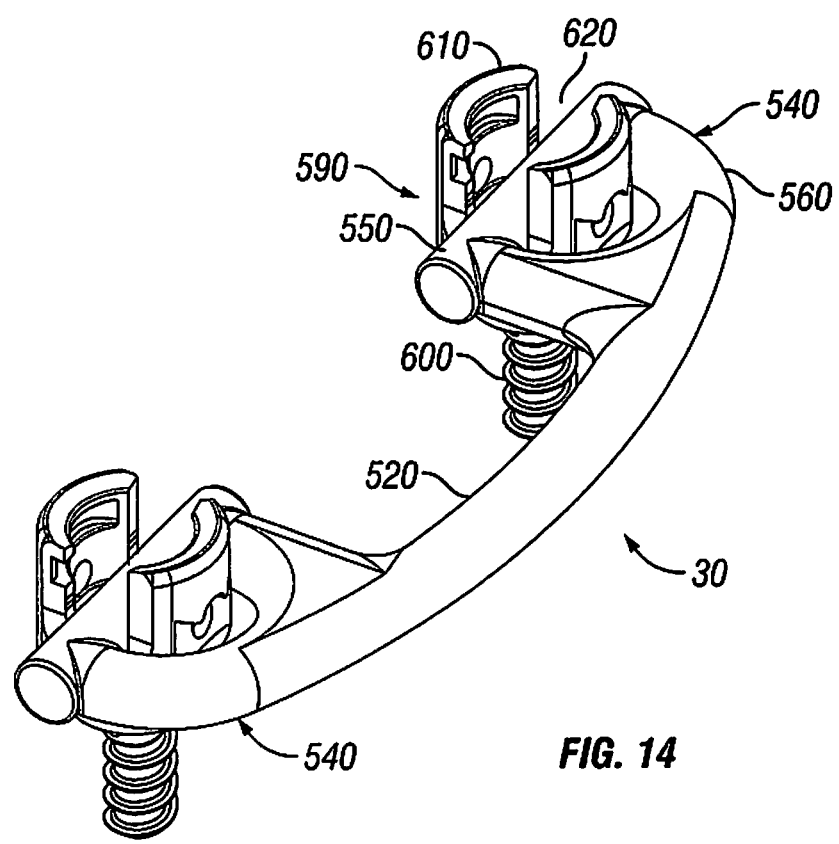
FIG. 14 is a perspective view of a dynamic spine stabilizer incorporating a convex bowed segment in accordance with one embodiment of the present invention.

FIGS. 13-14 illustrate dynamic stabilizer 30 in accordance with additional embodiments of the present invention. As illustrated, the dynamic stabilizer 30 may comprise a cross member (e.g., bowed segment 520) extending between first rod connecting end 530 and second rod connecting end 540. In an embodiment, the cross member may be made from a material comprising titanium or a titanium alloy. In the embodiment illustrated by FIG. 13, the bowed segment 520 may have a curvature that is inwardly concave. In an alternative embodiment illustrated by FIG. 14, the bowed segment 520 may be outwardly convex. When stress is applied to one or both of first rod connecting end 530 and the second rod connecting end 540, the bowed segment 520 should at least partially flex. In this manner, the dynamic stabilizer 30 should allow for relative movement between bone fasteners to which it is attached.

In the illustrated embodiment, first rod connecting end 530 may define an opening 545 formed by rod portion 550 and arch portion 560. As illustrated, the arch portion 560 may span from a first end 570 of the rod portion 550 to a second end 580 of the rod portion 550. In an embodiment, the bowed segment 520 generally may extend from the arch portion 560. The rod portion 550 may be configured and adapted for insertion into rod receiving members of corresponding bone fasteners. As illustrated by FIG. 14, bone fastener 590 may comprise head 610 with threaded portion 600 extending from one end of head 610. Head 610 may comprise slot 620 for receiving rod portion 550. After insertion of rod portion 550 into the slot 620, a locking element (e.g., a nut) may be placed onto the head 610 to secure the rod portion 550 in the slot 620.

Figure 15:
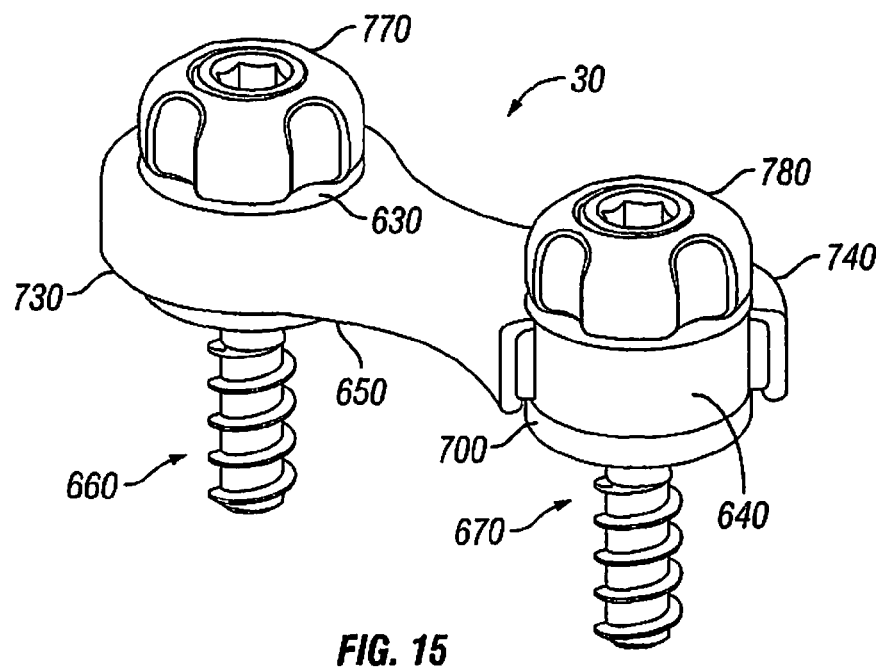
FIG. 15 is a perspective view of a dynamic spine stabilizer incorporating one or more compressible elements in accordance with one embodiment of the present invention.

FIG. 15 illustrate dynamic stabilizer 30 that incorporates one or more compressible elements 630, 640 in accordance with another embodiment of the present invention. As illustrated, dynamic stabilizer 30 includes cross member 650 for connecting a pair of bone fasteners 660, 670. In accordance with the present embodiments, the cross member 630 connects the bone fasteners 660 with the compressible elements 630, 640 providing for dynamic stabilization. More particularly, compression of the compressible elements 630, 640 when one or both of the bone fasteners 660, 670 moves should allow for at least some relative movement between the bone fasteners 660, 670. In an embodiment, the compressible elements 630, 640 may be generally ring-shaped sleeves that fit around the bone fasteners 660, 670.

Figure 16:
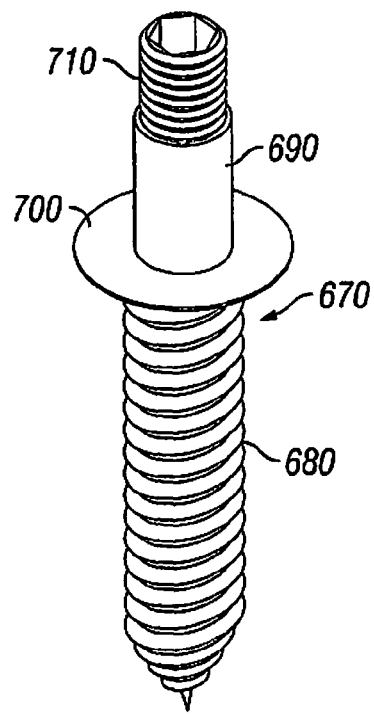
FIG. 16 is a top view of a cross member for use with the dynamic spine stabilizer of FIG. 15 in accordance with one embodiment of the present invention.

FIG. 16 illustrates one of the bone fasteners 660, 670 in more detail in accordance with an embodiment of the present invention. As illustrated, the bone fastener 670 may be a posted screw that comprises a threaded stem 680 for implantation into a bone, intermediate cylindrical portion 690, flange 700 for supporting one of the compressible elements 630, 640 on the cylindrical portion 690, and head 710. In an embodiment, the intermediate cylindrical portion 690 is not threaded. In an embodiment (not illustrated), intermediate cylindrical portion 690 may be threaded. One of the compressible elements 630, 640 (illustrated by FIG. 15) may be disposed around the cylindrical portion 690 supported by the flange 700. In an embodiment, the head 710 may be a threaded, cylindrical head.

Figure 17:
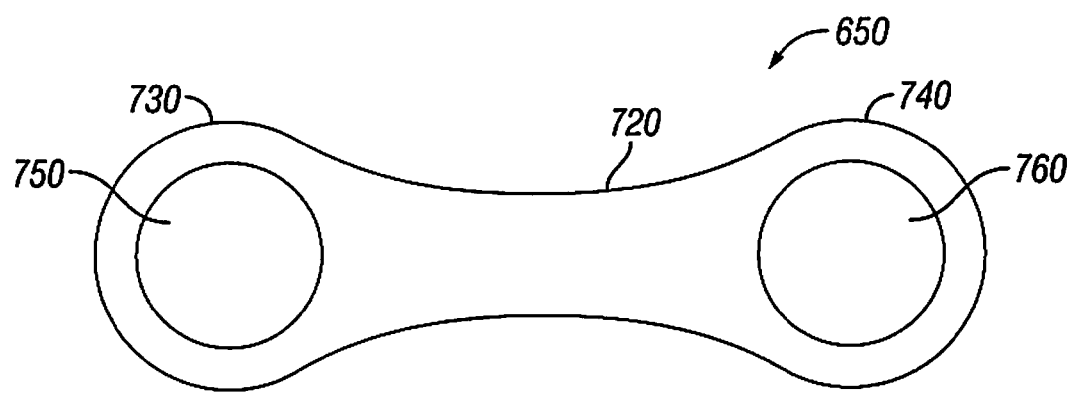
FIG. 17 is a perspective view of a bone fastener for use with the dynamic spine stabilizer of FIG. 15 in accordance with one embodiment of the present invention.

FIG. 17 illustrates the cross member 650 in more detail in accordance with an embodiment of the present invention. In an embodiment, the cross member 650 is made from a material that comprises titanium or a titanium alloy. As illustrated, the cross member 650 includes a tapered portion 720 that extends between first connecting end 730 and second connecting end 740. Each of the first connecting end 730 and the second connecting end 740 may comprise an opening 750, 760. As illustrated, the first and second connecting ends 730, 740 may be generally ring shaped. In an embodiment, the openings 750, 760 may be sized to fit over the corresponding one of the bone fasteners 640, 650. As illustrated by FIG. 15, each of the first connecting end 730 and the second connecting end 740 are disposed around a corresponding compressible element 630, 640. To secure the cross member 650 on the bone fasteners 660, 670, a locking element (e.g., nuts 770, 780) may be tightened onto the head 710 of each of the bone fasteners 660, 670.

Figure 18:
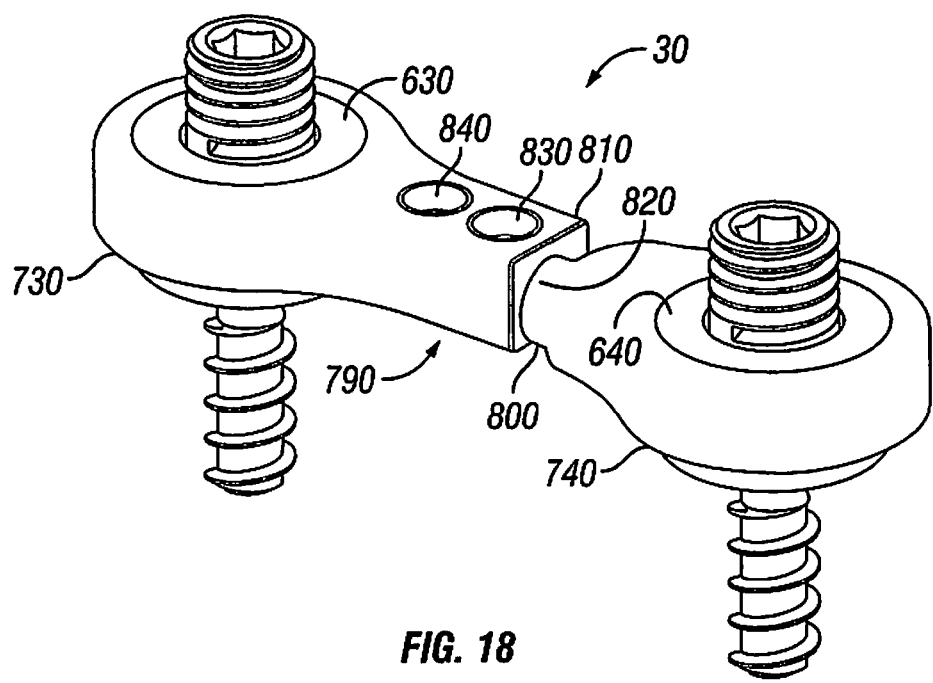
FIG. 18 is a perspective view of a dynamic spine stabilizer incorporating one or more compressible elements in accordance with another embodiment of the present invention.

FIG. 18 illustrates dynamic stabilizer 30 in accordance with another embodiment of the present invention. The illustrated dynamic stabilizer 30 is similar to the embodiment of FIG. 15, in that the dynamic stabilizer 30 incorporates one or more compressible elements 630, 640. However, unlike the cross member 630 of FIG. 15, the dynamic stabilizer 30 of FIG. 18 comprises an adjustable cross member 790 that has an adjustable length. As illustrated, the dynamic stabilizer 30 comprises an adjustable cross member 790 that extends between a first connecting end 730 and a second connecting end 740. The first connecting end 730 and the second connecting end 740 may be coupled to adjacent vertebrae (not illustrated) by bone fasteners 660, 670. Compressible elements 630, 640 should allow for at least some respective movement between the bone fasteners 660, 670. Dynamic stabilizer 30 further may comprise rod 800 that extends from second connecting end 740. In an embodiment, the rod 800 is circular in cross section. In another embodiment (not illustrated), the rod 800 is rectangular or square in cross section. As illustrated, the rod 800 may be integrally formed with the second connecting end 740. In an embodiment (not illustrated), the rod 800 is a separate piece coupled to the second connecting end 740. In the illustrated embodiment, the dynamic stabilizer 30 further comprises a rod connecting portion 810 that extends from the first connecting end 730. As illustrated, the rod connecting portion 810 may be integrally formed with the first connecting end 730. In an embodiment (not illustrated), rod connecting portion 810 is a separate piece coupled to the first connecting end 730. The rod connecting portion 810 may have an opening 820 that extends through a portion of the rod connecting portion 810. The opening 820 should receive the rod 800 extending from the second connecting end 740. Accordingly, the adjustable cross member 790 may comprise the rod connecting portion 810 having the rod 800 disposed in the opening 820 of the rod connecting portion 810. To adjust the length of the adjustable cross member 790, the depth that the rod 800 is inserted into the opening 820 may be varied. The rod connecting portion 810 may comprise one or more openings 830, 840 for receiving set screws to secure the rod 800 in the opening 820, preventing movement of the rod 800 with respect to the rod connecting portion 810.

Figure 19:
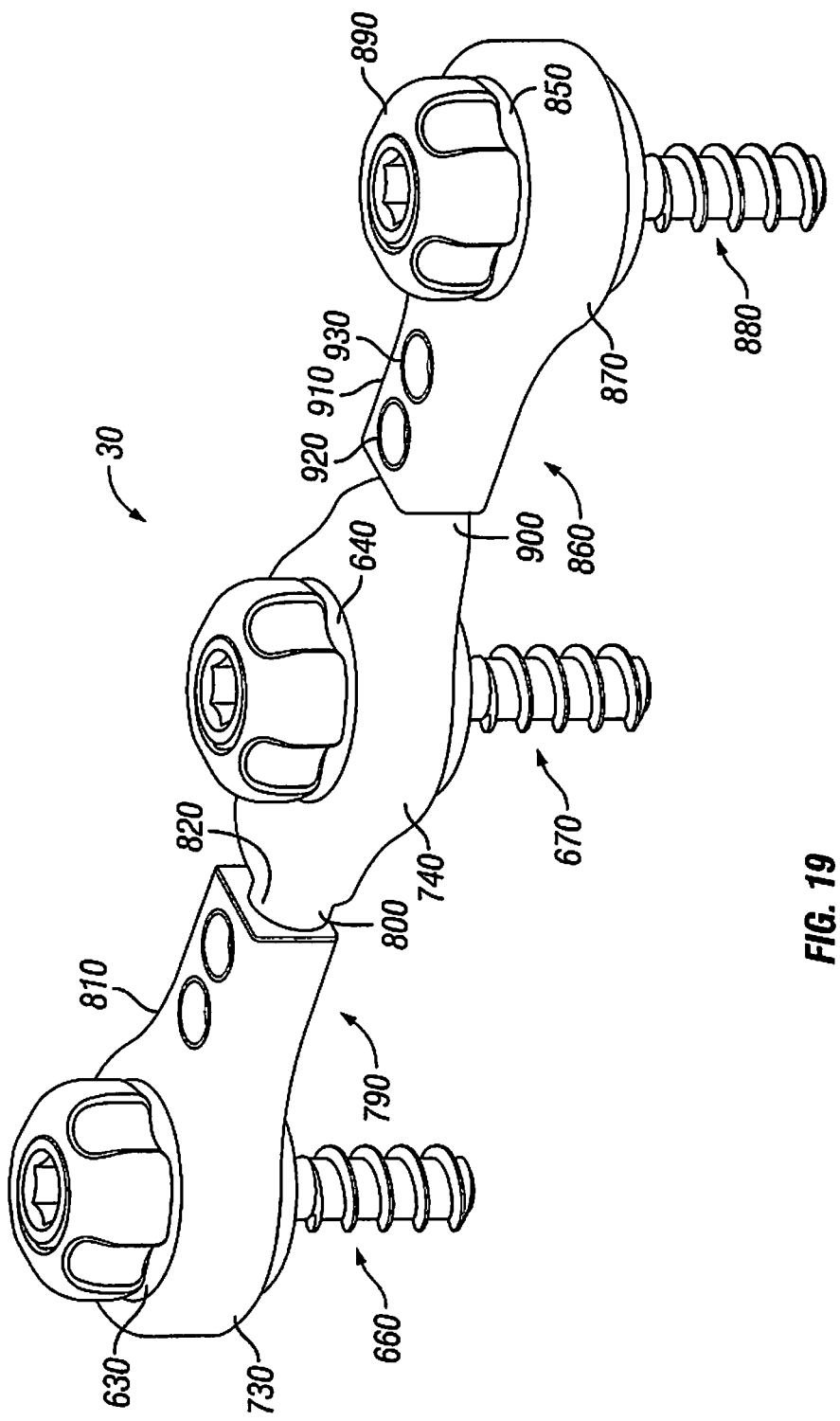
FIG. 19 is a perspective view of a dynamic spine stabilizer incorporating one or more compressible elements in accordance with another embodiment of the present invention.

FIG. 19 illustrates dynamic stabilizer 30 in accordance with another embodiment of the present invention. The illustrated dynamic stabilizer 30 is similar to the embodiment of FIG. 18, in that the dynamic stabilizer 30 incorporates one or more compressible elements 630, 640, 850. However, unlike the dynamic stabilizer 30 of FIG. 17 which can dynamically stabilize one level of the patient's spine, the dynamic stabilizer 30 of FIG. 19 is configured and adapted to stabilizer more than one level of a patient's spine. To span more than one level in a patient's spine, the dynamic stabilizer 30 comprises adjustable cross member 790 for spanning a first level of a patient's spine, and second adjustable cross member 860 for spanning a second level of the patient's spine. As illustrated, the adjustable cross member 790 extends between the first connecting end 730 and the second connecting end 740. The first connecting end 730 and the second connecting end 740 may be coupled to adjacent vertebrae (not illustrated) by bone fasteners 660, 670. Compressible elements 630, 640 should allow for at least some respective movement between the bone fasteners 660, 670. The first connecting end 730 may include a rod connecting end 810 having an opening 800 for receiving a rod 800. As illustrated, the rod 800 may extend from the second connecting end 740. To adjust the length of the adjustable cross member 790, the depth that the rod 800 is inserted into the opening 820 may be varied. In this manner, the adjustable cross member 790 may span across a first level of a patient's spine.

As illustrated by FIG. 19, the second adjustable cross member 860 extends between the second connecting end 740 and the third connecting end 870. In the illustrated embodiment, the third connecting end 870 is disposed around compressible element 850, which is disposed on the bone fastener 880. Compressible element 850 may be disposed around an intermediate portion of bone fastener 880. A locking element (e.g., nut 890) may be placed onto the bone fastener 880 to secure the third connecting end 870 on the bone fastener 880. In an embodiment, compressible element 850 may be a generally ring-shaped sleeve that fits around the bone fastener 880. As illustrated, second rod 900 may extend from the second connecting end 740 in the opposite direction of rod 800. In addition, second rod connecting portion 910 may extend from the third connecting end 870. The second rod connecting portion 910 may have an opening (not illustrated) that extends through a portion of the second rod connecting portion 910. The opening should receive the second rod 900 extending from the second connecting end 740. Accordingly, the second adjustable cross member 860 may comprise the second rod connecting portion 910 having the second rod 900 disposed in the opening of the second rod connecting portion 910. To adjust the length of the second adjustable cross member 860, the depth that the second rod 900 is inserted into the opening may be varied. In addition, the second rod connecting portion 910 may comprise one or more openings 920, 930 for receiving set screws to secure the second rod 900 in the opening, preventing movement of the second rod 900 with respect to the second rod connecting portion 910. However, the compressible elements 640, 850 should allow for respective movement between the bone fasteners 670, 880 interconnected by the second adjustable cross member 860.

While it is apparent that the invention disclosed herein is well calculated to fulfill the objects stated above, it will be appreciated that numerous modifications and embodiments may be devised by those skilled in the art.

What is claimed is:

1. A spine stabilization system, comprising:
a first bone fastener configured to attach the spine stabilization system to a first vertebra;
a second bone fastener configured to attach the spine stabilization system to a second vertebra;
a dynamic spine stabilizer configured to connect the first bone fastener and the second bone fastener with at least some relative movement between the first bone fastener and the second bone fastener; and
a rod portion attachable to the dynamic spine stabilizer, wherein when a force is applied to the dynamic spine stabilizer, the dynamic stabilizer is capable of sliding in lateral direction along the rod portion and is capable of sliding in a direction generally perpendicular to the lateral direction.

2. The dynamic spine stabilizer of claim 1, wherein the dynamic spine stabilizer includes a translatable end defining an opening for receiving the rod portion.

3. The dynamic spine stabilizer of claim 2, wherein the translatable end comprises a yoke disposed around the rod portion.

4. The dynamic spine stabilizer of claim 2, wherein the rod portion is secured to the translatable end with a clamp laterally offset from the dynamic spine stabilizer.

5. The dynamic spine stabilizer of claim 4, wherein the translatable portion is positioned in between the clamp and a pedicle screw.

6. The dynamic spine stabilizer of claim 5, wherein the translatable portion is configured to freely move between the clamp and the pedicle screw.

7. The dynamic spine stabilizer of claim 2, wherein the translatable end is configured to rotate with respect to the rod portion.

8. The dynamic spine stabilizer of claim 1, wherein the dynamic spine stabilizer includes a rod-locking end defining a seat configured to receive a second rod portion.

9. The dynamic spine stabilizer of claim 1, wherein the dynamic spine stabilizer includes a tapered segment positioned between a translatable end and a rod-locking end.

10. A dynamic spine stabilizer comprising:
a first rod configured for attachment to a first bone fastener;
a second rod configured for attachment to a second bone fastener;
a cross member extending between the first rod and the second rod, wherein the cross member comprises a first end fixedly coupled to the first lateral rod, and a translatable end disposed around the second rod, wherein the translatable end is movable with respect to the second rod, and wherein when a force is applied in a direction of a longitudinal axis of the cross member, the cross member is capable of movement along its longitudinal axis and wherein when a force is applied in a direction oblique or perpendicular to the longitudinal axis of the cross member, the cross member is capable of sliding in a direction generally oblique or generally perpendicular to the longitudinal axis.

11. The dynamic spine stabilizer of claim 10, wherein translatable end comprises a yoke disposed around the second rod.

12. The dynamic spine stabilizer of claim 10, wherein the second rod comprises a flanged end for securing the translatable end on the second rod.

\* \* \* \* \*